Figure 2:
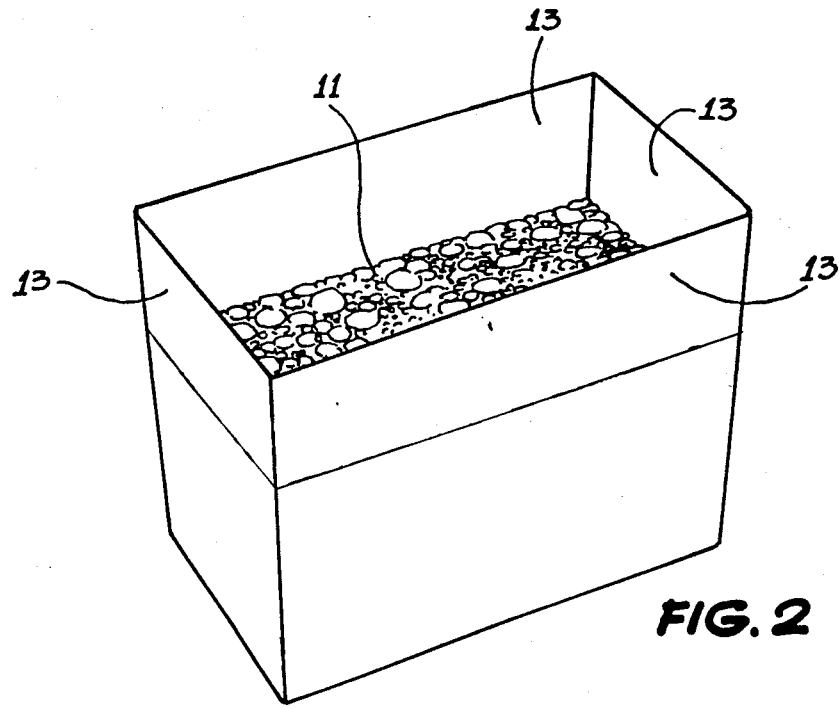

United States Patent [19]

Murphy

[11] Patent Number: 4,738,684
[45] Date of Patent: Apr. 19, 1988

[54] FUEL BRIQUETTE

[76] Inventor: Patrick Murphy, 4 Ard na Malahide, Malahide, County Dublin, Ireland

[21] Appl. No.: 7,323

[22] Filed: Jan. 27, 1987

[30] Foreign Application Priority Data

Jan. 28, 1986 [IE] Ireland ................................. 1894/85

[51] Int. Cl.$^4$ .......................... C10L 5/36; C10L 11/06
[52] U.S. Cl. ...................................................... 44/591
[58] Field of Search ................ 44/38, 40, 41, 14, 10 E

[56] References Cited

U.S. PATENT DOCUMENTS

| 270,298 | 1/1883 | FRX | 44/40 |
| 739,131 | 9/1903 | Adler | 44/40 |
| 849,915 | 4/1907 | McDonough | 44/40 |
| 1,401,803 | 12/1921 | Lynes | 44/40 |
| 2,011,245 | 8/1935 | Horne | 44/40 |
| 2,206,362 | 7/1940 | Mulcey | 44/40 |
| 2,227,256 | 12/1940 | Haffner | 44/41 |
| 2,548,379 | 4/1951 | Lammersen | 44/40 |

*Primary Examiner*—Carl F. Dees
*Attorney, Agent, or Firm*—Ladas & Parry

[57] ABSTRACT

A fuel briquette (10) comprises compacted moistened coal slack or dross particles (11) sealed in a waterproof combustible envelope (12). The particles (11) substantially fill the volume of the envelope.

4 Claims, 1 Drawing Sheet

FUEL BRIQUETTE

This invention relates to a fuel briquette.

Coal is a widely used domestic fuel. In the production of coal, however, from both open cast and deep mines approximately sixty per-cent of the total production is slack or dross with only about forty per-cent of the total production being solid coal lumps which are suitable for domestic or industrial use. The slack or dross produced has only a limited commercial use, for example, it is used in addition to coal as a domestic fuel, however, this use is in general extremely small compared with the amount of slack produced from coalfields.

The main problem with burning slack in a domestic fire is that since the slack particles are small they tend to choke the fire. Also, the slack is difficult to handle in a domestic situation.

Thus, it is an object of the invention to provide a means by which slack or dross can be conveniently used as a fuel, particularly in a domestic fire.

According to the invention there is provided a fuel briquette characterised by compacted moistened coal slack or dross particles sealed in a waterproof combustible envelope, said particles substantially filling the volume of the envelope.

The waterproof combustible envelope is preferably a waterproof paperboard container. An example of a known type of suitable paperboard container is a carton of the type used for packaging milk or other beverages.

The coal slack or dross preferably comprises a mixture of particles of varying sizes up to 40 mm in diameter.

The briquette preferably has a water content of up to twelve per-cent by weight.

In another embodiment of the invention the coal slack may be moistened by waste oil or diesel fuel, to provide a briquette which burns faster. Also, if desired the mixture of slack particles may contain a minor amount of sawdust, wood chippings or particles of peat or other combustible particles.

It has been found that the waterproof paperboard container tends to burn slowly on a domestic fire and the moisture in the slack helps to fuse the slack together so that by the time the paperboard container has burned off the coal slack has substantially fused together to form a solid mass of coal.

Figure 1:
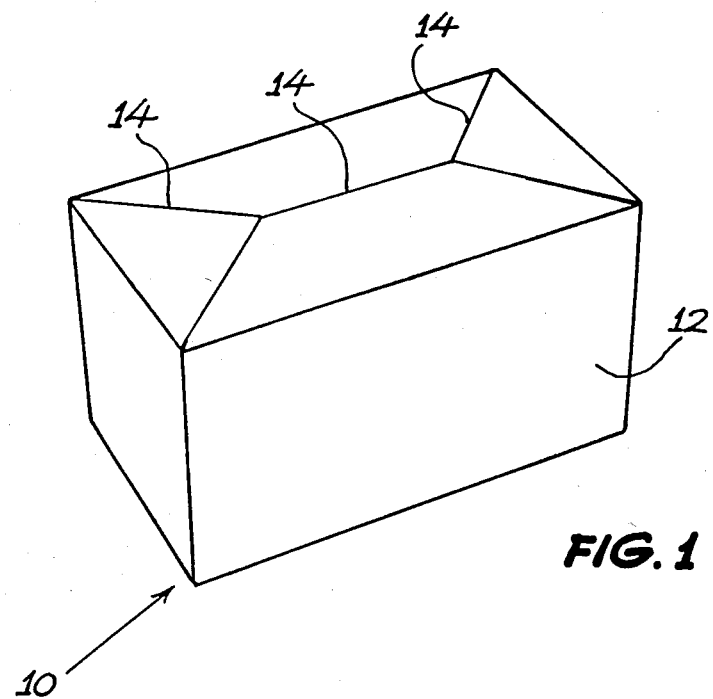

An embodiment of the invention will now be described, by way of example, with reference to the accompanying drawings, in which, FIG. 1 is a perspective view of a fuel briquette according to the invention and FIG. 2 is a perspective view of the briquette of FIG. 1 with the envelope open.

Referring now to the drawings, wherein similar numerals have been used to indicate like parts, there is shown therein a fuel briquette according to the invention generally indicated at 10. The briquette 10 comprises compacted moistened slack or dross particles 11, which are sealed in a waterproof paperboard container 12. The slack or dross particles 11 comprise a mixture of particle sizes of up to approximately 40 mm in diameter. It is preferable to have a variety of particle sizes so that there are as few as possible interstitial spaces in the mixture. The briquette 10 is moistened with and contains up to twelve per-cent (12%) by weight of water. Further, the slack particles substantially fill the interior volume of the container 12 when it is closed. The container 12 has end flaps 13 which have suitable fold lines 14 so that the end flaps 13 can be folded over one another and sealed in conventional manner to seal the top of the container.

In use, a briquette 10 according to the invention is simply placed on a fire. The waterproof paperboard envelope 12 is slow burning and thus the moistened slack 11 is subject to the high temperatures of the fire for a time before the envelope burns off. During this time the heat from the fire causes the slack particles to substantially fuse together to form a solid mass of coal which does not choke the fire. The moisture in the slack mixture enhances the clinging of the slack particles 11 to one another and it also helps in the fusing of the slack particles together when subject to heat from the fire.

The briquette 10 is clean and easy to produce, store and distribute, whereas bags of loose slack are extremely difficult to handle. The briquettes according to the invention have been found to burn well in a manner similar to a lump of coal. As the container 12 is waterproof it may be readily displayed or stored in wet conditions if necessary.

I claim:

1. A fuel briquette comprising a sealed waterproof combustible container substantially completely filled with compacted coal slack or dross moistened with water, wherein the container comprises an inherently stiff waterproof paperboard material, and wherein the slack or dross has a water content of up to 12% by weight in an amount sufficient to cause the slack or dross to fuse together into a coherent mass by the time the container burns away.

2. A fuel briquette as claimed in claim 1, wherein the particles are of varying sizes of up to 40 mm in diameter.

3. A fuel briquette as claimed in claim 1, wherein the briquette includes waste oil or diesel fuel.

4. A fuel briquette as claimed in claim 1, wherein the briquette includes a minor amount of other combustible particles.

* * * * *